(12) United States Patent
Nettesheim et al.

(10) Patent No.: US 10,143,510 B2
(45) Date of Patent: Dec. 4, 2018

(54) ASSEMBLY FOR TREATING WOUNDS

(71) Applicant: relyon plasma GmbH, Regensburg (DE)

(72) Inventors: Stefan Nettesheim, Regensburg (DE); Dariusz Korzec, Wenzenbach (DE); Dominik Burger, Alteglofsheim (DE)

(73) Assignee: Relyon Plasma GmbH, Regensburg (DE)

(*) Notice: Subject to any disclaimer, the term of this patent is extended or adjusted under 35 U.S.C. 154(b) by 64 days.

(21) Appl. No.: 15/180,213

(22) Filed: Jun. 13, 2016

(65) Prior Publication Data
US 2016/0287310 A1 Oct. 6, 2016

Related U.S. Application Data

(63) Continuation of application No. PCT/IB2014/066837, filed on Dec. 12, 2014.

(30) Foreign Application Priority Data

Dec. 12, 2013 (DE) .......................... 10 2013 113 941

(51) Int. Cl.
*A61B 18/04* (2006.01)
*H05H 1/24* (2006.01)
*A61N 1/44* (2006.01)

(52) U.S. Cl.
CPC .............. *A61B 18/042* (2013.01); *A61N 1/44* (2013.01); *H05H 1/24* (2013.01);
(Continued)

(58) Field of Classification Search
CPC .......... A61B 18/042; A61N 1/44; H05H 1/24; H05H 2001/2381; H05H 2001/2481; A61M 2205/3592; A61M 2205/584
See application file for complete search history.

(56) References Cited

U.S. PATENT DOCUMENTS

| 3,903,891 A * | 9/1975 | Brayshaw ............ A61B 18/042 313/231.31 |
| 7,605,340 B2 * | 10/2009 | Duan ........................ H05H 1/34 219/121.49 |

(Continued)

FOREIGN PATENT DOCUMENTS

| DE | 202008008980 | 10/2008 |
| DE | 102007054161 | 5/2009 |

(Continued)

*Primary Examiner* — Lauren P Farrar
(74) *Attorney, Agent, or Firm* — Simpson & Simpson PLLC

(57) ABSTRACT

The invention relates to an assembly for treating wounds and to a hand held unit for treating wounds. The assembly and the hand held unit comprise a device for producing a plasma and/or an excited gas or gas mixture by means of a piezo-electric transformer, which is housed together with a circuit board in a housing of the device, and the assembly comprises an expansion element. A control circuit, to which the piezoelectric transformer is electrically connected, is realized on the circuit board. A second end of the expansion element surrounds a wound region to be treated. A first end of the expansion element is detachably connected to the housing of the device at the opening of the housing. The produced plasma and/or excited gas or gas mixture thus enters the expansion element from the opening of the housing.

17 Claims, 3 Drawing Sheets

(52) U.S. Cl.
CPC ............... *A61M 2205/3592* (2013.01); *A61M 2205/584* (2013.01); *H05H 2001/2481* (2013.01)

(56) References Cited

U.S. PATENT DOCUMENTS

| | | | |
|---|---|---|---|
| 8,267,884 B1* | 9/2012 | Hicks | A61B 18/042 315/111.21 |
| 2008/0237484 A1* | 10/2008 | Morfill | H05H 1/30 250/427 |
| 2012/0215158 A1* | 8/2012 | Barthel | A61B 18/042 604/26 |
| 2013/0069530 A1* | 3/2013 | Watson | A61M 16/12 315/111.21 |
| 2013/0204244 A1* | 8/2013 | Sakakita | A61B 18/042 606/40 |
| 2013/0226073 A1* | 8/2013 | Kummerfeld | A61L 2/14 604/23 |

FOREIGN PATENT DOCUMENTS

| | | |
|---|---|---|
| DE | 102009041167 | 3/2011 |
| DE | 102010015899 | 8/2011 |
| DE | 102011001416 | 9/2012 |
| DE | 102012003563 | 8/2013 |
| DE | 102012103362 | 10/2013 |
| DE | 102013107448 | 1/2015 |
| EP | 0957793 | 11/1999 |
| KR | 20130023588 | 3/2013 |
| WO | 2002032332 | 4/2002 |
| WO | 2010034451 | 4/2010 |
| WO | 2011110342 | 9/2011 |
| WO | WO2012/005132 | 1/2012 |
| WO | 2012158443 | 11/2012 |
| WO | WO2012/178177 | 12/2012 |
| WO | 2013076102 | 5/2013 |

* cited by examiner

ASSEMBLY FOR TREATING WOUNDS

CROSS-REFERENCE TO RELATED APPLICATIONS

This application is filed under 35 U.S.C. § 111(a) and § 365(c) as a continuation of International Patent Application No. PCT/IB2014/066837, filed Dec. 12, 2014, which application claims priority from German Patent Application No. 10 2013 113 941.8, filed Dec. 12, 2013, which applications are incorporated herein by reference in their entireties.

FIELD OF THE INVENTION

The invention relates to an assembly for treating wounds. In particular the assembly for treating wounds includes a device for generating a plasma and/or an excited gas or gas mixture, respectively, with a piezoelectric transformer. The device has a housing in which the piezoelectric transformer along with a circuit board is arranged. On the circuit board a control circuit is realized, to which the piezoelectric transformer is electrically connected. A plasma generated with the device and/or the excited gas or gas mixture, respectively, exits from an opening of the housing.

BACKGROUND OF THE INVENTION

The German patent application DE 10 2013 107 448.0 discloses an apparatus for the reduction of germs by means of plasma. The dielectric film encloses an area to be sterilized (wound or object) with its peripheral edge. A high voltage end of the piezoelectric transformer is facing the outside of the dielectric film and the plasma is ignited within the dielectric film.

The German patent application DE 10 2012 103 362 A1 shows a plasma treatment device for treating the human body. The plasma treatment device is pen-shaped. To this end, a first electrode is provided in a pen portion. The pen portion is grounded in the area of the electrode. According to an embodiment a second electrode is provided, which is of circular shape and is placed on the portion of skin to be treated. The second electrode is for setting a distance. According to a second embodiment, a grounding cover is connected with the grounding conductor. In this way, by means of the grounding cover, also a constant distance to the skin portion can be set.

The Korean patent application KR 2013-0023588 relates to a plasma array, distanced from the wound to be treated by a distancing element.

The U.S. Pat. No. 8,267,884 B1 relates to a cylindrical housing of a plasma apparatus. A cap can be connected to the nozzle of the plasma apparatus. The cap can be removed and sterilized or disposed of.

The international patent application WO 02/32332 A1 discloses a chamber in contact with the skin surface to be treated. By means of a vacuum pump the generated and hot plasma is again extracted.

The German patent application DE 10 2012 003 563 A1 discloses an apparatus for the sterilizing treatment of wounds, with a housing, wherein in the housing a plasma generator for generating a sterilizing plasma is arranged. In the housing furthermore a flow module for generating a flow of gas is provided, the flow of gas forming a free jet carrying the sterilizing plasma out of the housing. A jet control unit is provided for purposefully affecting the free jet by controlling the gas flow generated by the flow module. According to an embodiment the wound is surrounded by a skirt with extraction openings, and an extraction port connects to an extraction duct.

The German patent application DE 10 2007 054 161 A1 discloses a method for sterilizing elongated work pieces. With the here described plasma treatment method a surface decontamination is achieved, in order to kill micro-organisms and viruses with a low-temperature plasma. The method distinguishes itself in that various suitable additives are mixed with the plasma, in order to achieve an as good as possible killing of the micro-organisms, or viruses, respectively. The method is applied to inorganic bodies.

The German patent application DE 10 2011 001 416 A1 discloses a plasma treatment apparatus for treating wounds or afflicted portions of skin. The plasma treatment apparatus has two flexible area electrodes for generating a non-thermal plasma. The two area electrodes each include at least one electric conductor, wherein the conductors are interwoven. At the outside of the area electrodes facing the surface to be treated, a wound contact layer of an antiseptically treated material is detachably fixed.

The international patent application WO 2010/034451 A1 discloses a plasma applicator for applying a non-thermal plasma to a surface, in particular for the plasma treatment of living tissue and in particular for the plasma treatment of wounds. The plasma applicator includes a cover lid for covering a part of the surface. In this way a cavity is formed between the cover lid and the surface. The non-thermal plasma is provided in the cavity, and in addition the cavity can be flushed with gas. Likewise a pump is provided which extracts gas from the cavity.

The international patent application WO 2012/158443 A2 discloses an apparatus for generating a cold plasma. The apparatus includes a handheld nozzle by which the plasma is directed to the spot to be treated for healing wounds, improving anomalies of the skin surface, and for killing germs.

In the international patent application WO 2011/110342 A1 a plasma treatment device for applying a non-thermal plasma through a plaster or a dressing, in order to achieve a plasma treatment of wounds, is disclosed. The plasma treatment device may be provided with a cover. In this case the plasma is generated at the outer surface of the cover.

The international patent application WO 2013/076102 A1 discloses an apparatus for generating a non-thermal plasma. A wall surrounds a reaction area, and by means of the wall the plasma source is also distanced from the surface. Elastic material is used for the distal portion of the wall, in order to achieve a sealing of the reaction area.

The German patent application DE 10 2010 015 899 A1 discloses an electrosurgical assembly with an electrosurgical instrument and a treatment device connected with the instrument. In the treatment device a current generator for providing HF-energy is provided. An embodiment of the electrosurgical instrument according to an embodiment has a conically widening front piece. Through an electrode a treatment fluid is supplied to the treatment spot. Thus here, during treatment, various separate instruments and devices are used.

The European patent EP 0 957 793 B1 discloses an endoscope with a flexible hollow tube attached to its distal end. In the hollow tube an electrode is arranged, connected, via a conduct, with a high frequency generator and an argon reservoir. Out of the distal end of the tube the ionized plasma is supplied to the treatment spot. In an embodiment the distal end of the tube is of conical shape.

In the US patent application US 2012/0215158 A1 an endoscope is disclosed, to which a cap-shaped front piece is attached. Within the front piece there is a plasma ignition apparatus, by which the supplied plasma can be ignited and supplied to the treatment spot.

The German patent application DE 10 2009 041 167 A1 discloses a multifunctional element for carrying out electro-surgical interventions. Within the multifunctional element there is an electrode connected to a high frequency generator providing high frequency current. At the same time the electrode serves as supply duct for fluid components.

SUMMARY OF THE INVENTION

It is an object of the invention to provide an assembly for treating wounds which is low-cost, easy to be used, and by which an efficient and safe treatment of wounds is possible. The above object is achieved by an assembly for treating wounds which has a device for generating a plasma and/or an excited gas or gas mixture. The device comprises a housing. A piezoelectric transformer is arranged in the housing. A circuit board, arranged in the housing encompasses a control circuit to which the piezoelectric transformer is electrically connected. An opening is formed in the housing towards which opening the high voltage end of the piezoelectric transformer is directed. A plasma generated with the device and/or the excited gas or gas mixture, respectively, exits from the opening of the housing. An expansion element is detachably connected with a first end to the housing of the device at the opening thereof. A second end of the expansion element surrounds a wound region to be treated. A cross-sectional area of the second end of the expansion element is larger than a cross-sectional area of the first end of the expansion element.

A further object of the invention is to provide a hand held unit for treating wounds which is low-cost, easy to be used, and by which an efficient and safe treatment of wounds is possible. The above object is achieved by a hand held unit for treating wounds which has a device for generating a plasma and/or an excited gas or gas mixture. The device comprises a housing. A piezoelectric transformer is arranged in the housing. A circuit board, arranged in the housing encompasses a control circuit to which the piezoelectric transformer is electrically connected. An opening is formed in the housing towards which opening the high voltage end of the piezoelectric transformer is directed. A plasma generated with the device and/or the excited gas or gas mixture, respectively, exits from the opening of the housing. An expansion element is detachably connected with a first end to the housing of the device at the opening thereof. A second end of the expansion element surrounds a wound region to be treated. A cross-sectional area of the second end of the expansion element is larger than a cross-sectional area of the first end of the expansion element.

In the assembly or the hand held unit according to the invention for treating wounds an expansion element is detachably mounted with a first end to the device for generating a plasma and/or an excited gas or gas mixture, respectively, in such a way that the opening of the housing of the device is led into the expansion element. With a second end the device surrounds a wound region to be treated. The device has a cross-sectional area at the second end of the expansion element which is larger than a cross-sectional area of the first end of the expansion element.

The device may be a plasma generator or ionizer or ozonizer. In case the device is an ionizer or ozonizer, instead of a plasma a gas mixture with excited molecules, ions, and reactive oxygen species, like for example ozone, atomic oxygen, H2O2, OH-radicals or NOx acts on the wound region. Strictly speaking it is not necessary for a plasma to reach the wound region. The effect on the surface of the wound region depends on the local concentration of the active gas species. As the active gas species react on the surface of the wound region, here an exchange of gas supported by the flow conditions must be enforced. Not only is the integral dose of the active gas species decisive for the effect, but it is also the maximal concentration at the surface of the wound region. A very high concentration applied over a short time is more effective than a low concentration applied over a long time. A short exposition in combination with a high concentration of the gas species results in a maximal surface activity.

A peripheral side surface of the expansion element has plural perforations. Via the perforations an exchange of gas or a pressure equilibration, respectively, between the interior of the expansion element and at least the environment is possible. At an interior side of the peripheral side surface at least one flow guiding element is arranged, so that a flow of plasma or excited gas or gas mixture, respectively, can be efficiently directed to the wound region to be treated.

A refeed for gas may connect the expansion element with the device. A color sensor may also be assigned to the expansion element, in order to indicate by a change of color that the treatment is complete. Furthermore, an RFID-chip may be assigned to the expansion element, so that, via the type of the expansion element and in connection with the device, at least a duration of the treatment is settable. By means of the RFID-chip it is possible to adapt the device in such a way that at least the strength and the duration of the generated plasma and/or of the excited gas or gas mixture, respectively, as the case may be the supply of additional gas (like for example argon) are adapted to the type of the expansion element.

According to the invention the device is a plasma generation device, provided with a piezoelectric transformer for generating the plasma. The high voltage end of the piezoelectric transformer is directed to the opening in the housing. The plasma generation device is a handheld device.

It is advantageous that the device is a handheld device. The handheld device is low-cost and assures easy handling. In combination with the expansion element a distance required for the respective treatment of the wound can be kept despite the handheld device. In addition, the expansion elements can be manufactured in a simple and cost efficient manner and with various configurations.

BRIEF DESCRIPTION OF THE DRAWINGS

Further advantages and advantageous embodiments of the invention are the subject of the following figures and their descriptions thereof in which.

DETAILED DESCRIPTION OF THE INVENTION

Identical reference numbers are used for like elements or elements of like functions of the invention. The embodiments shown are only one possibility how the assembly for treating wounds by means of a plasma may be configured. Although the following description exclusively refers to a device configured as a plasma generation device, this is not to be construed as a limitation of the invention. As already mentioned above, instead of a plasma also a gas mixture with excited molecules, ions and reactive oxygen species, like for example ozone, atomic oxygen, H2O2, OH-radicals, or NOx may bring about the effect in the treatment of wounds. Strictly speaking it is not necessary for plasma to reach the wound region.

Figure 1:
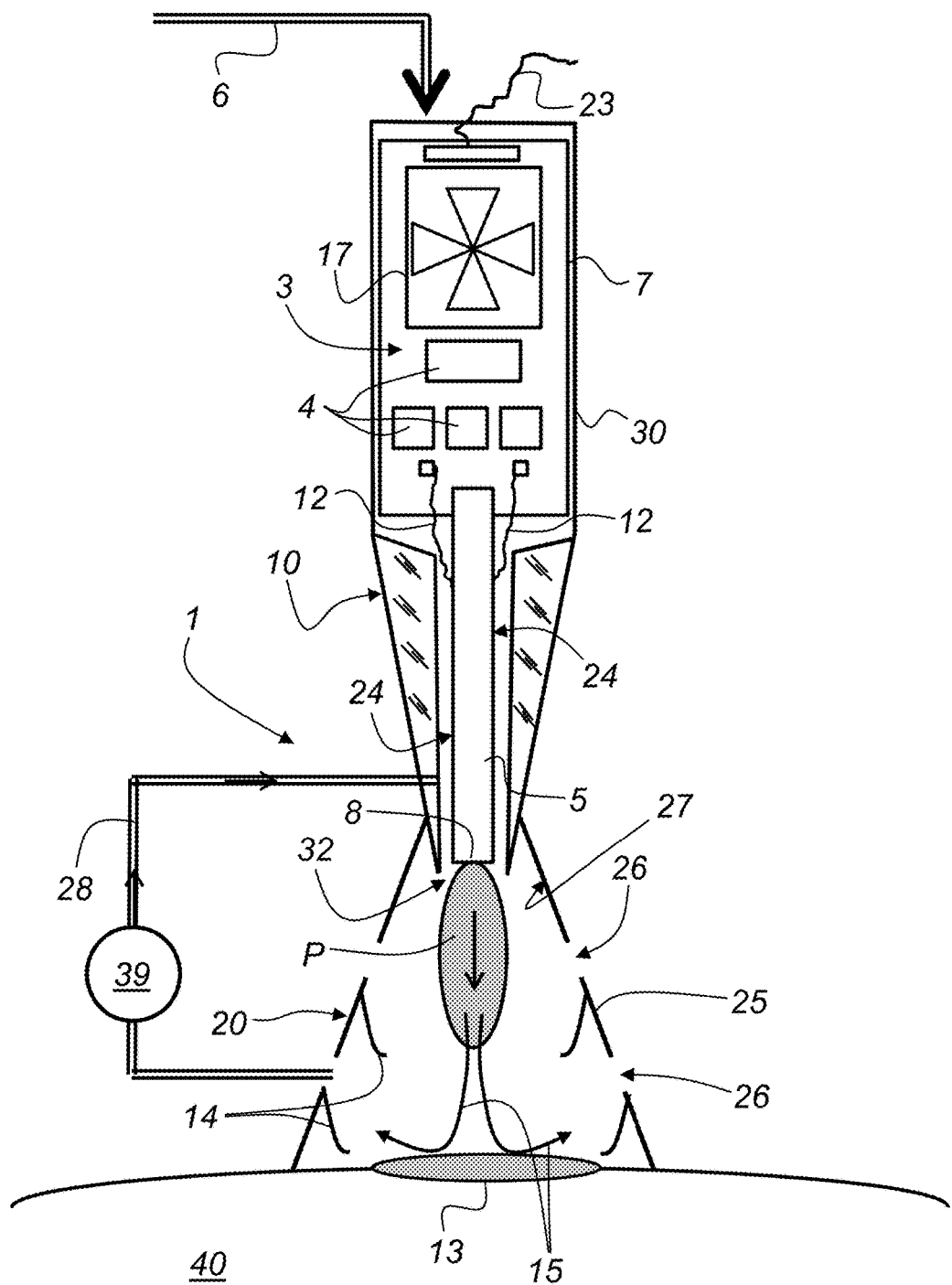
FIG. 1 is a schematic view of the principal setup of the assembly according to the invention for the plasma treatment of wounds.

A schematic view of assembly 1 for treating wounds according to the invention is shown in FIG. 1. In the embodiment shown here plasma P is generated in plasma generation device 10 with piezoelectric transformer 5. Piezoelectric transformer 5 is arranged in housing 30 of plasma generation device 10. It is evident to the skilled person that plasma P may also be generated in a different way rather than with piezoelectric transformer 5. Although the following description refers to piezoelectric transformer 5, this is not to be construed as a limitation of the invention. For controlling, piezoelectric transformer 5 is connected with circuit board 7. Circuit board 7, with a plurality of electronic elements 4, realizes control circuit 3. Through control circuit 3, it is possible to excite piezoelectric transformer 5 at its resonance frequency. Control circuit 3 for piezoelectric transformer 5 may be connected to an external power supply, which is a usual standard mains-adapter (not shown), connected via cable 23 with housing 30 of piezoelectric transformer 5. Likewise, the power supply can be via an accumulator. A combination of accumulator and standard mains-adapter is also conceivable. The control voltage is applied to respective side surface 24 of piezoelectric transformer 5 via respective electrical contact 12 by control circuit 3 of circuit board 7. Due to the excitation voltage applied to side surfaces 24 of piezoelectric transformer 5 the required high voltage is generated at high voltage end 8 of piezoelectric transformer 5. Furthermore, in or at housing 30 fan 17 may be provided, providing a flow of air within housing 30 towards opening 32 of housing 30. Likewise, via gas duct 6, gas or a gas mixture may be supplied to plasma generation device 10, with which the plasma is ignited by piezoelectric transformer 5.

Expansion element 20 is configured in such a way that it can be detachably connected with first end 21 (see FIG. 2) to housing 30 of plasma generation device 10. Second end 22 (see FIG. 2) of expansion element 20 is configured to enclose wound region 13 to be treated with peripheral edge 29 (see FIG. 2) of second end 22. Also, expansion element 20, at the peripheral edge 29, is in contact with body part 40 on which wound region 13 to be treated is located. In order for plasma flow 15 to spread in expansion element 20 and provide an effective treatment of wounded area 13, second end 22 of expansion element 20 has cross-sectional area 19 (see FIG. 3) which is larger than cross-sectional area 18 (see FIG. 3) at first end 21 of expansion element 20.

In order to keep the pressure inside expansion element 20 approximately at the pressure level of the environmental pressure, a peripheral side surface 25 of expansion element 20 has plural perforations 26. Via perforations 26, the excess reaction gas and the reaction products can escape. At the opening 32 of the housing 30, i.e., in the region of first end 21 of expansion element 20, there is a high flow velocity. Thereby, via the Venturi effect, environmental gas (air) can be aspirated at the suitably arranged perforations 26 of expansion element 20.

For improved formation of plasma flow 15 within expansion element 20 at least one flow guiding element 14 is arranged at interior side 27 of peripheral side surface 25. Plasma flow 15 is to be formed such that it is directed to wound region 13 to be treated and has an optimized interaction time with wound region 13 to be treated. Likewise, refeed 28 may be provided, connecting expansion element 20 and plasma generation device 10. According to a further embodiment, refeed 28 may be coupled to a pump, in order to enforce an active recirculation. The circulation may be up to a ratio of 10:1 of the input volume stream to the circulation volume stream. Via refeed 28 gas from within expansion element 20 can thus be supplied specifically to plasma generation device 10. Preferentially the gas is directed into the region of high voltage end 8 of piezoelectric transformer 5.

Figure 2:
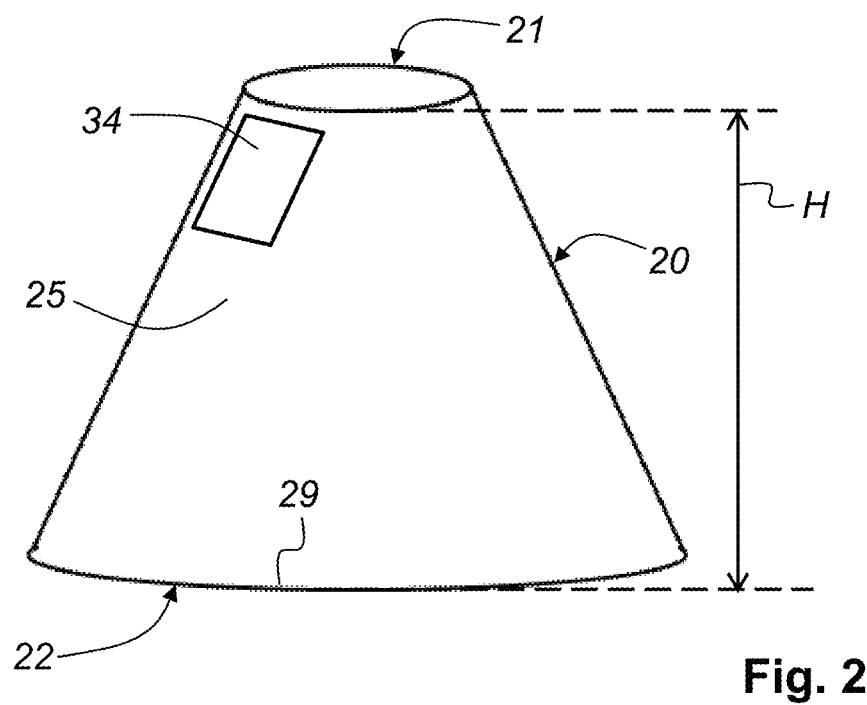
FIG. 2 is a perspective view of an embodiment of an expansion element used together with the plasma generation device.

In FIG. 2 a possible embodiment of expansion element 20 is shown. As already mentioned in the description of FIG. 1, expansion element 20 is detachably connected via first end 21 with plasma generation device 10 (see FIG. 1). Although the following description refers to expansion element 20 which is funnel-shaped, this is not to be construed as a limitation of the invention. It is obvious to the skilled person that the shape of expansion element 20 is irrelevant for the usability in the present invention.

Figure 3:
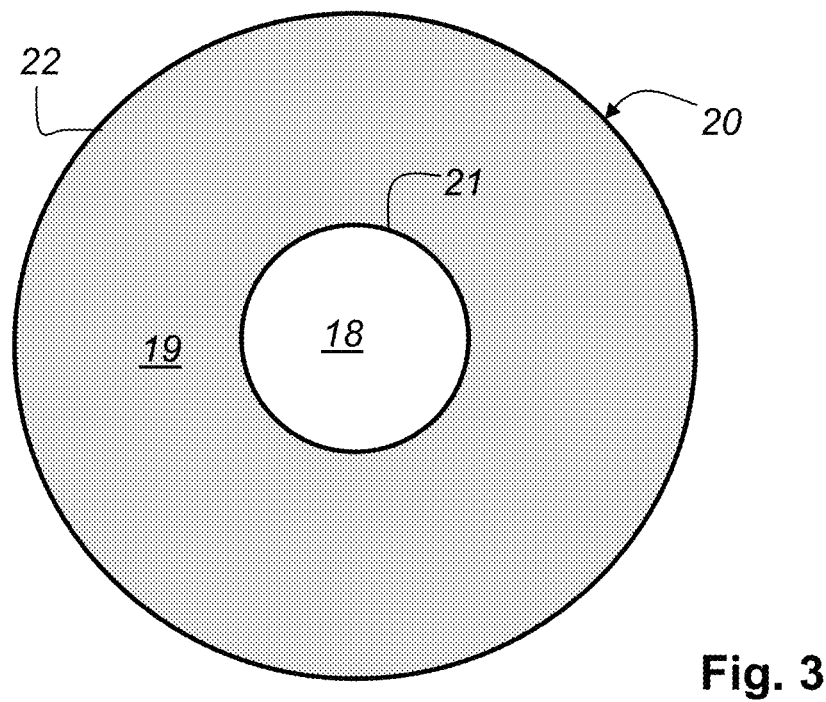
FIG. 3 is a top view of the expansion element.

An important condition for the use of expansion element 20 is, as shown in FIG. 3, that expansion element 20 at first end 21 has cross-sectional area 18 which is smaller than cross-sectional area 19 of second end 22 of expansion element 20. Furthermore, peripheral edge 29 of expansion element 20 at second free end 22 should be of such dimensions that it surrounds wound region 13 to be treated. Additionally, cross-sectional area 18 at first end 21 of expansion element 20 should correspond to the shape of plasma generation device 10 in the region of opening 32 of housing 30, so that expansion element 20 can be mounted detachably and in a form-locked manner to housing 30 of plasma generation device 10. Furthermore, expansion element 20 may be provided with RFID-chip 34, in order for plasma generation device 10 to be able to read the type of expansion element 20 and to make corresponding settings of plasma generation device 10 via the control circuit. Furthermore, via RFID-chip 34, height H of expansion element 20 may be read. Height H represents the distance of plasma generation device 10 from wound region 13 to be treated. Height H also is a parameter to be set for plasma generation device 10.

Figure 4:
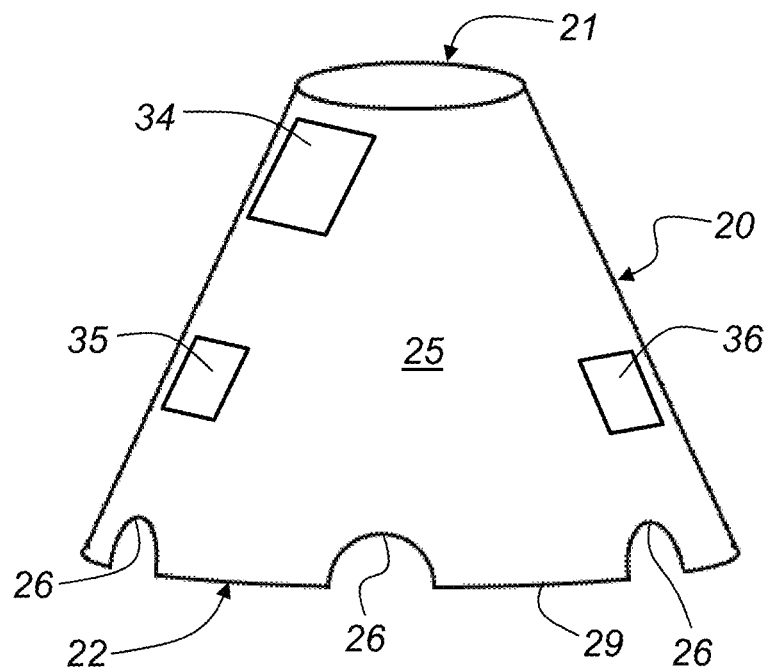
FIG. 4 is a perspective view of a further embodiment of the expansion element; and, FIG. 5 is a perspective view of an additional embodiment of the expansion element.

FIG. 4 shows a perspective view of a further embodiment of expansion element 20. Here, in addition to RFID-chip 34 and peripheral side surface 25 of expansion element 20, color sensor 35 and ozone sensor 36 are assigned. With color sensor 35, it can be indicated that the treatment of wound region 13 is completed. It is obvious that RFID-chip 34, color sensor 35, and ozone sensor 36 can be assigned to peripheral side surface 25 of expansion element 20 alone and/or in arbitrary combination. Expansion element 20 shown here has plural perforations 26 at peripheral edge 29.

Figure 5:
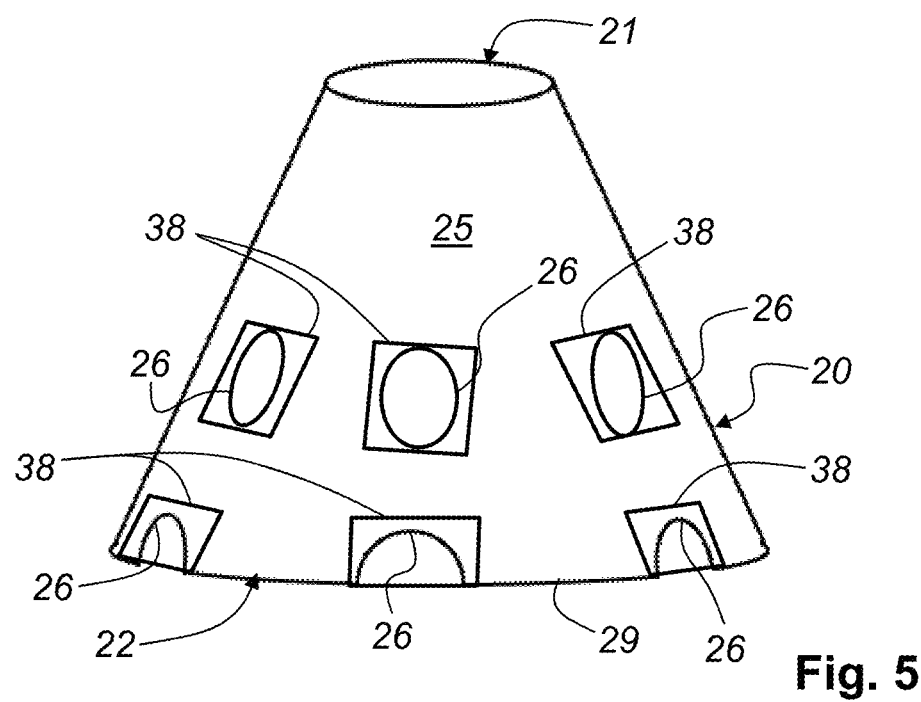

FIG. 5 shows a further possible embodiment of expansion element 20. Expansion element 20 shown here not only has plural perforations 26 at peripheral edge 29, but also on peripheral side surface 25. Each perforation 26 is covered by filter 28, so that only those gas components can exit which are to be removed from within expansion element 20, and which, as the case may be, are to be supplied to a re-use.

It is particularly advantageous if expansion element 20 is configured as single-use element. A disinfection process can be avoided, as expansion element 20 is disposed of after each use. Expansion element 20 may be manufactured in a low-cost manner by injection molding or deep drawing or thermoforming. It is obvious that expansion element 20 may be provided in various configurations. At a maximal configuration expansion element 20 has plural perforations 26, each provided with filter 38. In addition, there is RFID-chip 34, color sensor 35, and ozone sensor 36. It is obvious to the skilled person that the maximal configuration is not a limitation of the invention.

LIST OF REFERENCE NUMERALS

1 Assembly
3 Control Circuit
4 Electronic Elements
5 Piezoelectric Transformer
6 Gas Duct
7 Circuit Board
8 High Voltage End
10 Plasma Generation Device
11 Peripheral Edge
12 Electrical Contact
13 Wound Region
14 Flow Guiding Element
15 Plasma Flow
17 Fan
18 Cross-sectional Area of First End
19 Cross-sectional Area of Second End
20 Expansion Element
21 First End
22 Second End
23 Cable of Mains-Adapter
24 Side of Piezoelectric Transformer
25 Peripheral Side Surface
26 Perforations
27 Interior Side
28 Refeed
29 Peripheral Edge
30 Housing
32 Opening
34 RFID-chip
35 Color Sensor
36 Ozone Sensor
38 Filter
39 Pump
40 Body Part
H Height
P Plasma

What is claimed is:

1. An assembly for treating wounds having a device for generating a plasma and/or an excited gas or gas mixture, wherein the device comprises:
    a housing;
    a piezoelectric transformer arranged in the housing;
    a circuit board arranged in the housing, the circuit board including a control circuit, to which the piezoelectric transformer is electrically connected;
    an opening formed in the housing towards which a high voltage end of the piezoelectric transformer is directed;
    a fan arranged in or at the housing to provide a flow of air within the housing towards the opening, wherein the plasma and/or the excited gas or gas mixture, respectively, generated with the device exits from the opening; and,
    an expansion element, including:
        a first end removably connected to the housing at the opening; and,
        a second end arranged to surround a wound region to be treated, wherein a cross-sectional area of the second end is larger than a cross-sectional area of the first end.

2. The assembly as recited in claim 1, wherein the expansion element further comprises a peripheral side surface including a plurality of perforations.

3. The assembly as recited in claim 2, further comprising at least one flow guiding element arranged at an interior side of the peripheral side surface, so that a flow of the plasma and/or the excited gas or gas mixture, respectively, is directed at the wound region to be treated.

4. The assembly as recited in claim 1, further comprising a refeed arranged to connect the expansion element and the device.

5. The assembly as recited in claim 1, wherein the expansion element further comprises a color sensor operatively arranged to indicate, by a change of color, that the treatment is completed.

6. The assembly as recited in claim 1, wherein the expansion element further comprises a RFID-chip, so that via the type of the expansion element and in connection with the device, at least a duration of the treatment is settable.

7. The assembly as recited in claim 1, wherein the expansion element further comprises an ozone-sensor.

8. The assembly as recited in claim 1, wherein each of the plurality of perforations comprises a respective filter.

9. A hand held unit for treating wounds having a device for generating a plasma and/or an excited gas or gas mixture, wherein the device comprises:
    a housing;
    a piezoelectric transformer arranged in the housing;
    a circuit board arranged in the housing, the circuit board including a control circuit, to which the piezoelectric transformer is electrically connected;
    an opening formed in the housing towards which a high voltage end of the piezoelectric transformer is directed;
    a fan arranged in or at the housing to provide a flow of air within the housing toward the opening, wherein the plasma and/or the excited gas or gas mixture, respectively, generated with the device exits from the opening; and,
    an expansion element, including:
        a first end detachably connected to the housing at the opening; and,
        a second end arranged to surround a wound region to be treated.

10. The hand held unit as recited in claim 9, wherein the expansion element further comprises a peripheral side surface including a plurality of perforations.

11. The hand held unit as recited in claim 10, further comprising at least one flow guiding element arranged at an interior side of the peripheral side surface, so that a flow of the plasma and/or the excited gas or gas mixture, respectively, is directed toward the wound region to be treated.

12. The hand held unit as recited in claim 9, further comprising a refeed arranged to connect the expansion element and the device.

13. The hand held unit as recited in claim 9, wherein the expansion element further comprises a color sensor operatively arranged to indicate, by a change of color, that the treatment is completed.

14. The hand held unit as recited in claim 9, wherein the expansion element further comprises a RFID-chip, so that via the type of the expansion element and in connection with the device, at least a duration of the treatment is settable.

15. The hand held unit as recited in claim 9, wherein the expansion element further comprises an ozone-sensor.

16. The hand held unit as recited in claim 9, wherein each of the plurality of perforations comprises a respective filter.

17. The hand held unit as recited in claim 9, wherein:
a first cross-section taken proximate the first end has a first cross-sectional area; and,
a second cross-section taken proximate the second end has a second cross-sectional area, the second cross-sectional area being greater than the first cross-sectional area.

\* \* \* \* \*